United States Patent
Mitchell

(10) Patent No.: US 10,987,365 B2
(45) Date of Patent: *Apr. 27, 2021

(54) COMPOSITIONS AND METHODS FOR THE TREATMENT OF PAIN

(71) Applicant: GM Pharmaceuticals, Inc., Arlington, TX (US)

(72) Inventor: Odes W. Mitchell, Arlington, TX (US)

(73) Assignee: GM Pharmaceuticals, Inc., Arlington, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/043,722

(22) Filed: Oct. 1, 2013

(65) Prior Publication Data

US 2014/0094438 A1 Apr. 3, 2014

Related U.S. Application Data

(60) Provisional application No. 61/708,533, filed on Oct. 1, 2012.

(51) Int. Cl.

| | |
|---|---|
| *A61K 31/616* | (2006.01) |
| *A61K 31/60* | (2006.01) |
| *A61K 31/522* | (2006.01) |
| *A61K 31/194* | (2006.01) |
| *A61K 31/137* | (2006.01) |
| *A61K 31/505* | (2006.01) |
| *A61K 31/4402* | (2006.01) |
| *A61K 31/495* | (2006.01) |
| *A61K 31/09* | (2006.01) |
| *A61K 31/045* | (2006.01) |
| *A61K 31/125* | (2006.01) |
| *A61K 31/167* | (2006.01) |
| *A61K 31/135* | (2006.01) |

(52) U.S. Cl.
CPC .......... *A61K 31/616* (2013.01); *A61K 31/045* (2013.01); *A61K 31/09* (2013.01); *A61K 31/125* (2013.01); *A61K 31/135* (2013.01); *A61K 31/137* (2013.01); *A61K 31/167* (2013.01); *A61K 31/194* (2013.01); *A61K 31/4402* (2013.01); *A61K 31/495* (2013.01); *A61K 31/505* (2013.01); *A61K 31/522* (2013.01); *A61K 31/60* (2013.01)

(58) Field of Classification Search
None
See application file for complete search history.

(56) References Cited

U.S. PATENT DOCUMENTS

| | | | | |
|---|---|---|---|---|
| 3,197,370 | A * | 7/1965 | Hanus | A61K 31/44 514/161 |
| 4,466,960 | A * | 8/1984 | Silverman et al. | 424/719 |
| 4,906,478 | A * | 3/1990 | Valentine | A61K 33/06 424/682 |
| 5,225,417 | A * | 7/1993 | Dappen | C07D 495/20 514/279 |
| 5,665,378 | A * | 9/1997 | Davis | A61K 9/7084 424/448 |
| 6,710,086 | B1 * | 3/2004 | Lai | A61K 47/555 514/423 |
| 2003/0105144 | A1 * | 6/2003 | Gao | A61K 9/0019 514/357 |
| 2003/0165436 | A1 * | 9/2003 | Staniforth | A61K 9/0075 424/46 |
| 2006/0083691 | A1 * | 4/2006 | Wermeling | A61K 9/0043 424/45 |
| 2007/0237816 | A1 * | 10/2007 | Finkelstein | 424/464 |
| 2009/0143463 | A1 * | 6/2009 | Takenaka | A61K 31/5578 514/468 |
| 2009/0175939 | A1 * | 7/2009 | Bosse et al. | 424/472 |
| 2010/0298258 | A1 * | 11/2010 | Mitchell | 514/52 |

OTHER PUBLICATIONS

Ellis GL, Delaney J, DeHart DA, Owens A. The efficacy of metoclopramide in the treatment of migraine headache. Ann Emerg Med. Feb. 1993;22(2):191-5 (abstract only).*
Waxler et al (Canadian J Anesth 51:685-689, 2004).*
Smith (Pain Physician 11:201-214, 2008).*
DeRuiter (Principles of Drug Action, 2:1-20, 2001) (Year: 2001).*
Monk et al (Drugs 36:286-313, 1988—Abstract only) (Year: 1988).*

* cited by examiner

*Primary Examiner* — Craig D Ricci
(74) *Attorney, Agent, or Firm* — Winstead PC

(57) ABSTRACT

The claimed invention relates to compositions that may be in a form of a liquid, solid, gel, cream or gel capsule comprising an analgesic, and methods for administering these compositions for treatment of patients suffering from various forms of pain.

5 Claims, No Drawings

COMPOSITIONS AND METHODS FOR THE TREATMENT OF PAIN

CROSS-REFERENCES TO RELATED APPLICATIONS

This Application claims the benefit under 35 U.S.C. § 119(e) of U.S. Provisional Patent Application No. 61/708,533 filed Oct. 1, 2012, which is incorporated herein by reference in its entirety as if fully set forth herein.

FIELD OF THE INVENTION

The present invention relates to compositions comprising an analgesic that may be in the form of a liquid, gel, cream, tablet or gel capsules, and methods for administering these compositions for treatment of patients suffering from various forms of pain.

BACKGROUND OF THE INVENTION

Pain is an unpleasant sensation with a wide range in severity that can be localized or prevalent throughout the body. Pain is affected by nerve stimulation that carries impulses to the brain and is a symptom of an underlying disease, disorder, or physical injury.

It is estimated that 100 million Americans currently suffer with pain. Clinical complaints due to pain come in many varieties. Such complaints may be due to such ailments as arthritis, back pain, neuropathy, or a headache.

A headache, also known as cephalalgia, ranks amongst the most common clinical pain complaints and can be caused from a wide variety of physiological effects. Such causes range from hormonal changes, muscle tension in the back of the neck, or from dehydration. Because headaches come in many forms, they may be treated or prevented by various methods. These methods may include maintaining a healthy lifestyle, reducing stress or making use of various medications. Such medications can be antianxiety drugs, antidepressants or nonsteroidal anti-inflammatories (NSAIDs). However, when these drugs are ineffective or not possible to use due to allergic reactions, other drug combinations may be prescribed.

SUMMARY OF THE INVENTION

An embodiment of the invention is directed to a composition comprising an analgesic/antipyretic compound. In certain embodiments of the invention, the composition further comprises an analgesic adjunct or an antihistamine. Embodiments of the invention provide for the composition as a liquid, solid, gel/cream, tablet or gel capsule.

DETAILED DESCRIPTION OF EXEMPLARY EMBODIMENTS

The present invention provides compositions and methods of using the compositions for the therapeutic treatment of pain. Specifically, the present invention comprises a composition of an analgesic/antipyretic either with or without an analgesic adjunct and either with or without an antihistamine, where said composition is in the form of a liquid, solid or gel/cream.

As used herein, the term "analgesic/antipyretic" refers to a compound or compounds that are effective in treating pain (analgesic) and are also effective at reducing fever (antipyretic).

In another embodiment of the present invention, the compositions may comprise an analgesic/antipyretic from one or more of the group consisting of acetaminophen, buprenorphine, butorphanol, codeine, dextropropoxyphene, dihydrocodeine, fentanyl, diamorphine (Heroin), hydrocodone, hydromorphone, ketobemidone, morphine, nalbuphine, oxycodone, oxymorphone, pentazocine, pethidine, tramadol, diflunisal, ethenzamide, aminophenazone, metamizole, phenazone, phenacetin, ziconotide, tetrahydrocannabinol, acetylsalicylic acid, choline salicylate, magnesium salicylate, sodium salicylate, ibuprofen, naproxen and ketoprofen.

In another embodiment of the present invention, the compositions may comprise an analgesic adjunct from one or more of the group consisting of S (+)-ketamine, metoclopramide, ciramadol, sulfentanil, caffeine and remifentanil.

The compositions of the present invention may be administered to the patient for oral use and may be in the form of an elixir, syrup and/or suspension according to an individual patient's preferences. In another embodiment of the present invention, the compositions may further comprise a flavorant.

In certain embodiments of the invention, the compositions of the claimed invention may be administered to the patient as a tablet, gel, cream or gel capsules.

In another embodiment of the present invention, the compositions may be substantially free of other added active ingredients. The other added active ingredient may comprise an antihistamine, such as one or more of the group consisting of diphenhydramine, cyproheptadine hydrochloride, brompheneramine, hydroxyzine, chlorpheniramine, pyrilamine maleate, pyrilamine tannate, acepromazine, aceprometazine, alimemazine, alimemazine tartrate, amoxydramine camsilate, antazoline chlorhydrate, antazoline mesilate, antazoline phosphate, astemizole, azatadine dimaleate, azelastine hydrochloride, bamipine hydrochloride, benactyzine hydrochloride, bretylium tosilate, bromazine hydrochloride, brompheniramine maleate, buclizine dihydrochloride, bufexamac, carbinoxamine maleate acid, cetiedil citrate, cetirizine dihydrochloride, chlorcyclizine hydrochloride, chlorphenamine maleate, chlorphenoxamine hydrochloride, chlorprothixene hydrochloride, cinnarizine, clemastine fumarate, clemizole hexachlorophenate, clemizole penicilline, clemizole undecylenate, clocinizine dihydrochloride, clofedanol, clofenetamine hydrochloride, cyclizine hydrochloride, dexchlorpheniramine maleate, di (acefylline) diphenhydramine, difencloxazine, dimelazine hydrochloride, dimenhydrinate, dimethoxanate hydrochloride, cimetotiazine mesilate, diphenhydramine hydrochloride, diphenhydramine mesilate, diphenylpyraline hydrochloride, diproqualone camsilate, dixyrazine, doxylamine succinate, eprozinol dihydrochloride, etodroxizine dimaleate, etybenzatropine bromhydrate, etybenzatropine hydrochloride, etymemazine hydrochloride, fenethazine hydrochloride, fenoxazoline hydrochloride, fenpentadiol, flunarizine hydrochloride, flupentixol decanoate, flupentixol dihydrochloride, histapyrrodine hydrochloride, hydroxyzine dihydrochloride, hydroxyzine embonate, indoramine hydrochloride, isothipendyl hydrochloride, ketotifene fumarate, levocabastine hydrochloride, levomepromazine, levomepromazine hydrochloride, levomepromazine embonate, levomepromazine maleate, loratadine, maprotiline hydrochloride, maprotiline mesilate, maprotiline resinate, meclozine hydrochloride, mecysteine hydrochloride, medifoxamine fumarate, mefenidramium metilsulfate, mepyramine maleate, mequitazine, methaqualone, methdilazine hydrochloride, metixene hydrochloride, mizolastine, moxisylyte hydrochloride, niaprazine, orphenadrine hydrochloride, oxaflumazine disuccinate, oxatomide, oxolamine benzilate, oxolamine citrate, oxomemazine, oxomemazine hydrochloride, parathiazine teoclate, perimetazine, pheniramine maleate, phenoxybenzamine hydrochloride, phenyltoloxamine, phenyltoloxamine citrate, pimethixene, pipotiazine, pipretecol dihydrochloride, pizotifene malate, prednazoline, profenamine hydrochloride, promethazine, promethazine hydrochloride, promethazine embonate, promethazine polyvinylbenzene-metacrylate, propiomazine, terfenadine, thenalidine tartrate, thenyldiamine hydrochloride, thiazinamium metilsulfate, thonzylamine hydrochloride, tripelennamine hydrochloride, triprolidine hydrochloride, and tymazoline hydrochloride, and combinations thereof.

In another embodiment, the compositions of the present invention may comprise one or more of about 1 mg to 1500 mg of an analgesic/antipyretic, 1 mg to 200 mg of an analgesic adjunct and 1 mg to 200 mg of an antihistamine. In certain embodiments of the invention, the compositions may comprise from about 435 mg to 1,338 mg of an analgesic/antipyretic.

In certain embodiments of the invention, the analgesic adjunct is caffeine. In certain embodiments of the invention, the antihistamine is diphenhydramine citrate. In other embodiments of the invention, the antihistamine is either diphenhydramine hydrochloride or Pyrliamine Maleate.

In another embodiment of the present invention, the compositions may be administered to a patient to treat and/or alleviate the occurrence or negative effects from one or more of the group consisting of chronic pain and acute pain.

In certain embodiments of the invention, the compositions of the invention are dissolved in solvents containing one or more buffering salts. Examples of these buffers include, but are not limited to, calcium carbonate, magnesium oxide, magnesium carbonate, aluminum hydroxide and sodium hydroxide. The use of one or more of these salts causes the analgesic/antipyretic, analgesic adjunct and antihistamine compounds to stay in solution.

In other embodiments of the invention, the compositions of the invention comprise simethicone. Simethicone is an orally administered anti-foaming agent used to reduce bloating, discomfort or pain caused by excessive gas.

In certain embodiments of the invention, the compositions of the invention comprise a diuretic agent. In some embodiments of the invention, the diuretic agent is pamabrom, which is a 1:1 mixture of 2-amino-2-methyl-1-propanol and 8-bromotheophyllinate.

In another embodiment of the present invention, the compositions may be administered to a patient to treat and/or alleviate the occurrence or negative effects of headaches. Compositions of the invention are formulated as a liquid in order to facilitate efficient absorption particularly by older individuals.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

WORKING EXAMPLES

The products listed below exemplify certain of the products in accordance with the claimed invention. In the products listed below, only the primary active ingredients, i.e., analgesic/antipyretic, analgesic adjunct or antihistamine is listed. It would be apparent to one of ordinary skill in the art that the listed product formulations could contain inert ingredients such as buffers, fillers and other inactive ingredients.

Product 1
Choline Salicylate 870 mg
Caffeine 65 mg
Product 2
Choline Salicylate 870 mg
Diphenhydramine Citrate 76 mg
Product 3
Choline Salicylate 870 mg
Product 4
Acetylsalicylic acid 845 mg
Caffeine 65 mg
Product 5
Acetylsalicylic acid 1000 mg
Caffeine 65 mg
Product 6
Choline Salicylate 1,338 mg
Caffeine 65 mg
Product 7
Choline Salicylate 870 mg
Diphenhydramine HCl 76 mg
Product 8
Choline Salicylate 1,338 mg
Diphenhydramine HCl 50 mg
Product 9
Choline Salicyate 1,338 mg
Diphenhydramine Citrate 76 mg
Product 10
Choline Salicylate 1,338 mg
Product 11
Choline Salicylate 870 mg
Chlophedianol HCl 25 mg
Thonzylamine HCl 100 mg/or Pyrliamine Maleate 50 mg/or Chlorcyclizine HCl 18.75 mg
Product 12
Choline Salicylate 1,338 mg
Pseudoephedrine HCl 60 mg
Pyrliamine Maleate 50 mg
Chlophendianol 25 mg
Product 13
Choline Salicylate 870 mg
Phenylephrine HCl 10 mg
Guaifenesin 400 mg
Product 14
Choline Salicylate 870 mg
Phenylephrine HCl 10 mg
Thonzylamine HCl 100 mg
Product 15
Choline Salicylate 870 mg
Caffeine 65 mg
Pyrliamine Maleate 15 mg
Product 16
Choline Salicylate 870 mg
Pamabrom 25 mg
Product 17
Choline Salicylate 870 mg
Pamabrom 25 mg
Pyrliamine Maleate 15 mg Product 18
Choline Salicylate 870 mg
Magnesium Salicylate 250 mg
Pamabrom 25 mg
Product 19
Choline Salicylate 870 mg
Magnesium Salicylate 250 mg
Caffeine 65 mg
Product 20
Choline Salicylate 435-1338 mg
Acetaminophen 250 mg
Product 21
Choline Salicylate 435-1338 mg
Acetaminophen 250 mg
Diphenhydramine Citrate (76 mg) or Diphenhydramine hydrochloride (50 mg)
Product 22
Choline Salicylate 435-1338 mg
Acetaminophen 250 mg
Pyrilamine Maleate 15 mg
Diphenhydramine Citrate (76 mg) or Diphenhydramine hydrochloride (50 mg)
Product 23
Choline Salicylate 435-1338 mg
Acetaminophen 250 mg
Caffeine 60 mg
Pyrilamine Maleate 15 mg
Product 24
Choline Salicylate 435 mg to 1,338 mg
Acetaminophen 1 mg to 1,000 mg
Caffeine 65 mg
Product 25 (Cream/Rub)
Choline Salicylate 435 mg to 1,338 mg
Menthol 10% by weight
Methyl Salicylate 30% by weight
Camphor 4% by weight
Product 26 (Liquid)
Acetaminophen 1 mg to 1000 mg
Caffeine 32 mg to 200 mg
Product 27 (Cream/Rub)
Choline Salicylate 435 mg to 1,338 mg
Trolamine Salicylate 10% by weight While specific embodiments of the present invention have been described, other and further modifications and changes may be made without departing from the spirit of the invention. All further and other modifications and changes are included that come within the scope of the invention as set forth in the claims. The disclosures of all publications cited above are expressly incorporated by reference in their entireties to the same extent as if each were incorporated by reference individually.

What is claimed is:

1. A composition comprising:
   (a) an analgesic/antipyretic combination comprising about 435 mg to about 1,338 mg choline salicylate and about 10 wt % trolamine salicylate based on the total weight of the composition;
   (b) at least one analgesic adjunct comprising about 1 mg to about 200 mg caffeine;
   (c) an antihistamine comprising about 1 mg to about 200 mg pyrilamine tannate;
   (d) a diuretic agent comprising pamabrom; and
   (e) an antifoaming agent comprising simethicone;
   wherein the composition is a cream.

2. The composition of claim 1, wherein said composition further comprises a flavorant.

3. The composition of claim 1, wherein an amount of the caffeine is 60 mg.

4. The composition of claim 1, wherein an amount of the caffeine is 65 mg.

5. The composition of claim 1, wherein the composition is dissolved in a buffering salt.

\* \* \* \* \*